United States Patent [19]

Vlahov et al.

[11] 4,290,862

[45] Sep. 22, 1981

[54] METHOD FOR THE PREPARATION OF NARWEDINE-TYPE ENONES

[75] Inventors: Radoslav Y. Vlahov; Dikran A. Krikoryan; Maria S. Zagorova; Maya H. Ninova; Stoyan P. Parushev, all of Sofia, Bulgaria

[73] Assignee: Edinen Centar P Chimia, Sofia, Bulgaria

[21] Appl. No.: 94,352

[22] Filed: Nov. 14, 1979

[51] Int. Cl.$^3$ .................... C25B 3/00; C07D 221/18
[52] U.S. Cl. ................... 204/59 R; 204/75; 546/61
[58] Field of Search ............... 204/59 R, 78

[56] References Cited

U.S. PATENT DOCUMENTS 3,950,236 4/1976 Miller et al. .................... 204/78
4,233,121 11/1980 Szebenyi ........................ 204/59 R Primary Examiner—F. Edmundson

[57] ABSTRACT

A method for the preparation of narwedine-type enones involves electrochemical oxidation of diphenolic derivatives in an organic solvent medium containing a conductive salt at a potential ranging from 1.1 to 1.7 volts. The enones so obtained are of high purity and are produced in good yields.

2 Claims, No Drawings

METHOD FOR THE PREPARATION OF NARWEDINE-TYPE ENONES

This invention relates to a method for the preparation of narwedine-type enones. More particularly, the present invention relates to a method for the preparation of narwedine-type enones by electrochemical oxidation.

The narwedine-type enones are known compounds which may be employed as the starting material in the synthesis of Amaryllidaceae alkaloids. This end is normally attained by the oxidation of diphenolic derivatives. Unfortunately, such prior art procedures result in the formation of a large number of by-products which are difficult to separate and of little or no known use.

In accordance with the present invention, these prior art limitations are effectively obviated by a novel technique which results in the production of a high purity narwedine-type enone in high yields. The resultant enone may subsequently be transformed by chemical means into Amaryllidaceae alkaloids. Briefly, the invention involves forming the desired enones by the electrochemical oxidation of diphenolic derivatives of the general formula

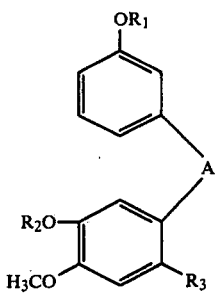

wherein A is selected from the group consisting of

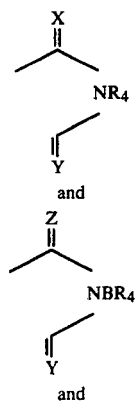

Z and Y are selected from the group consisting of $H_2$ and O, $R_1$, $R_2$ and $R_4$ are alkylic groups selected from the group consisting of $CH_2C_6H_5$ and $CH_2C_6H_4OCH_3$, X representing a halogen atom and B representing $HClO_4$ and similar salts of organic and inorganic acids.

The enones obtained in accordance with this oxidation are of the formula

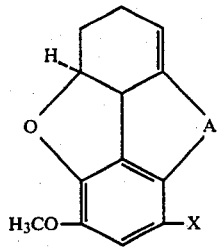

wherein A and X are as represented above.

The electrochemical oxidation herein described is effected in an electrolytic cell having separate anode and cathode compartments, and an organic solvent medium containing a conductive salt at a working potential ranging from 1.1 to 1.7 volts. The solvent medium found to be particularly useful for this purpose is methyl cyanate. Typical conductive salts suitable for this purpose are $LiClO_4$, $KClO_4$, $NaClO_4$, $(C_4H_9)_4NBF_4$ and $(C_2H_5)_4NBF_4$.

The working electrode chosen for use herein may be platinum, graphite and the like, the potential being measured by means of a reference electrode. The medium in which oxidation is effected may be maintained in either an acidic, alkaline or neutral condition by the use of additives such as $Na_2CO_3$, $K_2CO_3$, $NaHCO_3$, , $HBF_4$, $CH_3COOH$ and the like.

As indicated, the prime advantage of the described method resides in the high level of purity of the final product. Unreacted starting material found with the final product is readily separated and recycled for further use in the process. Yield is found to be of the order of 40%, such being higher than that attained by means of the known methods of chemical oxidation.

Examples of the invention are set forth below. It will be appreciated by those skilled in the art that these examples are for purposes of exposition only and are not intended to be limiting.

EXAMPLE 1

This example describes the preparation of 8-bromo-9-oxogalantaminon by electrolytic oxidation of N-methyl-(4'-methoxyphenethyl)-2-bromo-4-methoxy-5-benzyloxybenzamide in accordance with the following equation:

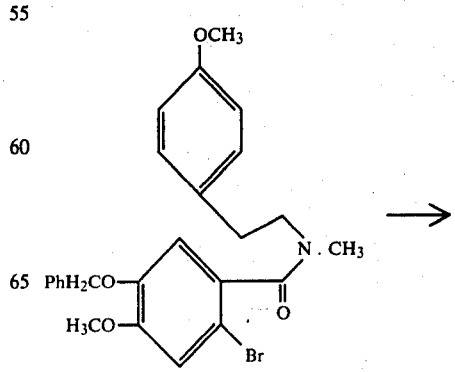

-continued

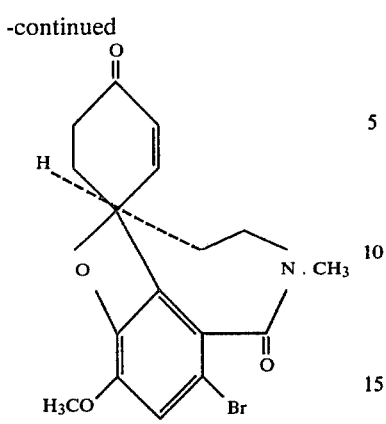

To the anode compartment of an electrolytic cell was added 0.001 mole of N-methyl-(4'-methoxyphenethyl)-2-bromo-4-methoxy-5-benzyloxybenzamide in a methyl cyanate solvent (benzamide to solvent ratio of 1:100) containing 2.4% $(C_4H_9)_4NBF_4$, a conductive salt, and 2% $HBF_4$ (acid) or $KClO_4$ and $K_2CO_3$. The cathode compartment and the electrolytic bridge of the reference electrode contained the anodic solvent and the same percentage of conductive salt. The working electrode was platinum and the reference electrode Ag-/Ag+ in methyl cyanate. The oxidation was carried out at 1.3 volts at a temperature below 0° C. until the equivalent electric charge has flown. This occurred within a time period of 3-5 hours. Following, the anode compartment was evaporated to dryness and the residue dissolved in chloroform and washed in bicarbonate solution and water. After drying the solution, the solvent was evaporated and the residue purified by chromatography or recrystallization. The yield of 8-bromo-9-oxogallantaminon was 40%.

EXAMPLE 2

This example describes the preparation of 8-bromo-9-oxogallantaminone by electrolytic oxidation of N-methyl-(4'-benzyloxyphenethyl)-2-bromo-4,5-dimethoxybenzamide in accordance with the following equation:

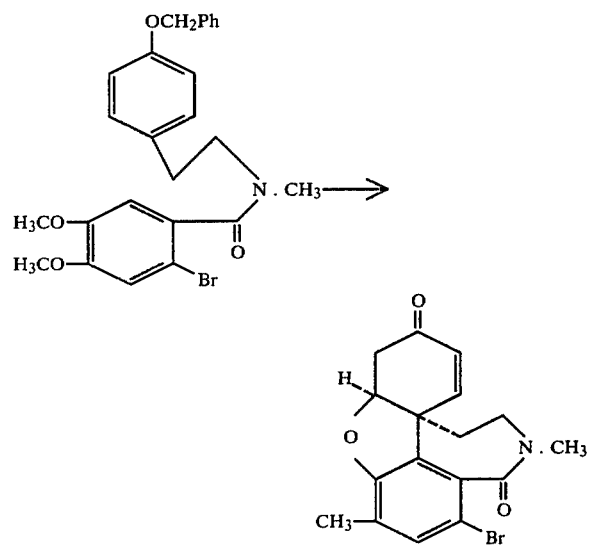

The procedure followed was that employed in Example 1 and the yield obtained of the desired oxogallantaminone was comparable thereto.

What is claimed is:

1. Method for the preparation of narwedine enones and derivates thereof of the formula

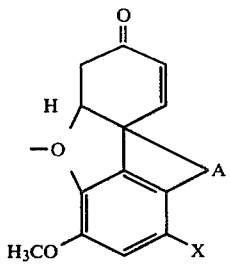

wherein A is selected from the group consisting of

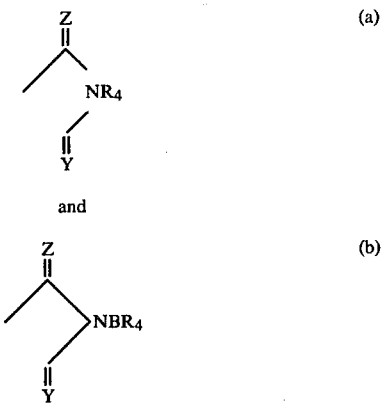

Z and Y being selected from the group consisting of $H_2$ and O, X being a halogen atom, $R_4$ a low order alkylic group selected from the group consisting of $CH_2C_6H_5$ and $CH_2C_6H_4OCH_3$ and B $HClO_4$ and related salts of organic and inorganic acids which comprises electrochemically oxidizing a diphenolic compound of the formula

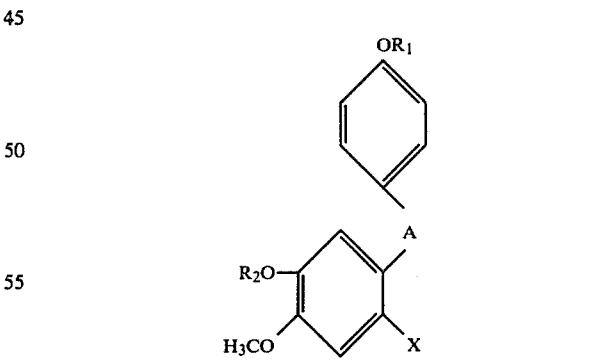

wherein A and X are as represented above and $R_1$, and $R_2$ are alkylic groups selected from the group consisting of $CH_2C_6H_5$ and $CH_2C_6H_4OCH_3$, said oxidizing being effected in a divided cell at an anode potential ranging from 1.1 to 1.7 volts in the presence of a solvent and a conductive salt.

2. Method in accordance with claim 1, wherein said conductive salt is selected from the group consisting of $KClO_4$, $LiClO_4$, $(C_4H_9)_4NBF_4$ and $(C_2H_5)_4NBF_4$.

* * * * *